United States Patent
Hytowitz

(10) Patent No.: US 8,083,353 B2
(45) Date of Patent: Dec. 27, 2011

(54) ANIMATED IMAGE VISION TEST

(76) Inventor: Allan N Hytowitz, Alpharetta, GA (US)

(*) Notice: Subject to any disclaimer, the term of this patent is extended or adjusted under 35 U.S.C. 154(b) by 0 days.

(21) Appl. No.: 12/583,225

(22) Filed: Aug. 17, 2009

(65) Prior Publication Data
US 2011/0037950 A1    Feb. 17, 2011

(51) Int. Cl.
*A61B 3/02* (2006.01)
(52) U.S. Cl. ........................................................ 351/239
(58) Field of Classification Search ............... 351/239
See application file for complete search history.

(56) References Cited

U.S. PATENT DOCUMENTS

| | | | |
|---|---|---|---|
| 3,807,839 A * | 4/1974 | Sugarman et al. | 351/243 |
| 4,257,690 A | 3/1981 | Howland | |
| 4,529,280 A * | 7/1985 | Nohda | 351/211 |
| 4,541,697 A * | 9/1985 | Remijan | 351/211 |
| 4,607,923 A | 8/1986 | Task | |
| 4,611,893 A | 9/1986 | Schrier | |
| 4,615,594 A | 10/1986 | Task | |
| 5,914,772 A * | 6/1999 | Dyer | 351/246 |
| 6,592,223 B1 * | 7/2003 | Stern et al. | 351/239 |
| 7,267,439 B2 * | 9/2007 | Toshima et al. | 351/223 |
| 7,350,921 B2 | 4/2008 | Ridings | |
| 7,367,675 B2 * | 5/2008 | Maddalena et al. | 351/237 |
| 7,396,128 B2 * | 7/2008 | Feher et al. | 351/205 |
| 7,429,109 B2 * | 9/2008 | Toshima et al. | 351/239 |
| 2006/0203195 A1 * | 9/2006 | Squire et al. | 351/211 |
| 2008/0309880 A1 * | 12/2008 | Fisher et al. | 351/239 |
| 2011/0001924 A1 * | 1/2011 | Giraudet et al. | 351/203 |

OTHER PUBLICATIONS

Wendy Strouse Watt, O.D., "Computer Vision Syndrome and Computer Glasses" http://www.mdsupport.org/library/cvs.html.

* cited by examiner

*Primary Examiner* — Ricky Mack
*Assistant Examiner* — Zachary Wilkes
(74) *Attorney, Agent, or Firm* — George R. Reardon

(57) ABSTRACT

Animated image vision tests take advantage of the ability of our eyes to detect both distance and motion. Moving images, such as rotating segmented circles, let the eyes detect motion as to the size, distance, and rotation direction of that moving image. That motion detection is much more precise than the interpretation of multiple static letters or static images. Using rotating images for vision testing rather than static images creates an acuity test more accurate than current tests, a test that is faster to use, and a test that doesn't require the ability to read.

1 Claim, 17 Drawing Sheets

ANIMATED IMAGE VISION TEST

CROSS-REFERENCE TO RELATED APPLICATIONS

The present non-provisional patent application claims the benefit of priority of U.S. Provisional Patent Application No. 61/188,197 which is entitled "Animated Image Vision Test" filed on Aug. 7, 2008, and which is incorporated in full by reference herein. The present invention relates generally to vision testing devices, methods, and more particularly to a novel method for more accurately testing vision and acuity related to the correctness of prescriptions for eyeglasses and contact lenses.

STATEMENT REGARDING FEDERALLY SPONSORED RESEARCH OR DEVELOPMENT

Not Applicable

REFERENCE TO SEQUENCE LISTING, A TABLE, OR A COMPUTER PROGRAM LISTING COMPACT DISK APPENDIX

Not Applicable

BACKGROUND OF THE INVENTION

The primary function of eyeglasses and contact lenses is in having the optical power of those lenses compensate for the loss of acuity (myopia) or excessive acuity (hyperopia) of the patient. Traditional vision acuity tests have used static optotypes as displays of printed or projected characters, objects, or shapes. Numerous patterns, configurations, and methods for static optotypes have been proposed for testing acuity based upon the ability of a subject to distinguish these various shapes, sizes, contrasts, and colors in tests such as Snellen charts, tumbling "E" arrays (static images of the letter "E" where the static image is also rotated 90 degrees, 180 degrees, and 270 degrees for discernment), Landolt "C" charts, and so on. Certain prior art vision testing patterns use periodic images, such as disks, rectangles, diamonds, etc.; others are quasi-periodic, such as tri-bar, and small checkerboard designs.

While the Landolt "C" chart is the clinical standard for acuity, the familiar Snellen eye testing chart as developed in 1862 using large, black, serifed letters on a white background is the test frequently used for determining visual acuity. The concept of these charts to verify acuity is based upon the patient seeing patterns such as letters or printed images on those charts, or as an image made visible by the reflection or projection of scattered light. Snellen's standard is that a person should be able to see and identify a 3.5 inch letter at a 20 foot distance (that ratio being consistent regardless of its use in the "English" or Metric system). This, however, assumes that the light is sufficiently bright so that the patient is able to identify the image and that there is sufficient contrast between the image and the background. A disadvantage of the Snellen type images is that even defocused letters can still be partially recognized by their blur patterns. Much time is thus wasted as the patient, whose eyes are being tested, attempts to guess the letter. The design of the Snellen chart is further complicated by each letter having a different degree of recognizability and by the tendency of the patient to strain to perceive coherency when trying to identify the letters. Additionally, the precision of the Snellen test is incumbent upon the individual identifying three of the five letters displayed at a 20 foot distance. Identification of less than three letters indicates insufficient refraction; however identification of more than three letters is actually over-refraction. These factors create a potential for both over-refraction and over-compensation.

Numerous other studies have shown difficulties with generating appropriate projected Snellen images as based upon technology developed in 1922 and updated in 1948. Projection systems are typically dependent upon a darkened room to enhance the contrast of the Snellen images, thereby creating a "contrast sensitivity" which may compromise actual acuity. Projection systems also inherently create a "fuzzy" image resulting from the mechanics of the diffraction of light waves, thus decreasing the accuracy of the perceived refraction.

Numerous attempts have been made to utilize recent technology to reproduce the Snellen test concept on computers or other devices with a high contrast display. Images from electronically generated characters, such as those from a cathode ray tube (CRT) or liquid crystal display (LCD), produce images that are distinctly sharper and less confusing than print or projected images. Such displays eliminate the inherent fuzziness of the Snellen test, but they still do not eliminate the tendency to misperceive letters and images inherent in focusing on significantly distant static images.

BRIEF SUMMARY OF THE INVENTION

A dynamic optotype is a rotating geometric figure, such as a segmented circle, a triangle, or other shape having dimensions and a rotation rate such that its motion can just be perceived at a specified viewing distance by a subject whose vision is or has been corrected to the accepted 20/20 standard. Unlike static optotype tests, the dynamic optotype acuity test utilizes the physiology and sensitivity of the photoreceptors in the eye to determine a precise acuity threshold instead of the subjective cognition of static images viewed at a fixed distance. The dynamic optotype concept is essentially the inverse of pixels being viewed on an electronic display whereby viewing those pixels at a sufficient distance causes the pixels to merge into an apparent image. The dynamic optotype motion lets the eye's photoreceptors function much as "screen pixels" where the detection of motion of the dynamic optotype creates an acuity threshold (the distance beyond which motion, either clockwise or counter-clockwise, is not perceivable) at a fixed arc degree width related to the diameter of the dynamic optotype, the gap width and gap height of the dynamic optotype, and the distance of the observer from that dynamic optotype.

In using the innate physiology of the photoreceptors, the dynamic optotype acuity threshold has numerous advantages over the subjective 60% accuracy and interpretation rate of the Snellen and other static optotype tests. Ironically, correctly identifying all of the letters of the Snellen test may result in a prescription too strong for mid-range reading or computer use. The increased accuracy of the dynamic optotype acuity test is not dependent upon the subjects' ability to read (regardless of the subjects' language or reading skills). The increased accuracy of the dynamic optotype test also tends to reduce the time spent attempting to interpret and comprehend the letters and shapes used in static optotype acuity tests, thus decreasing the time necessary to determine the correct acuity diagnosis.

Item 1—typical dynamic optotype image.
Item 2—left fixation point.
Item 3—right fixation point.
Item 4—benchmark fixation point separation of 26.2 cm.
Item 5—viewing distance.
Item 6—viewing direction towards the left fixation point.
Item 7—viewing direction towards the dynamic optotype.
Item 8—viewing direction towards the right fixation point.
Item 9—the 20 arc degree separation width of the fixation points when they are at a separation distance of 26.2 cm apart and viewed at a distance of 75 cm.

Figure 1:
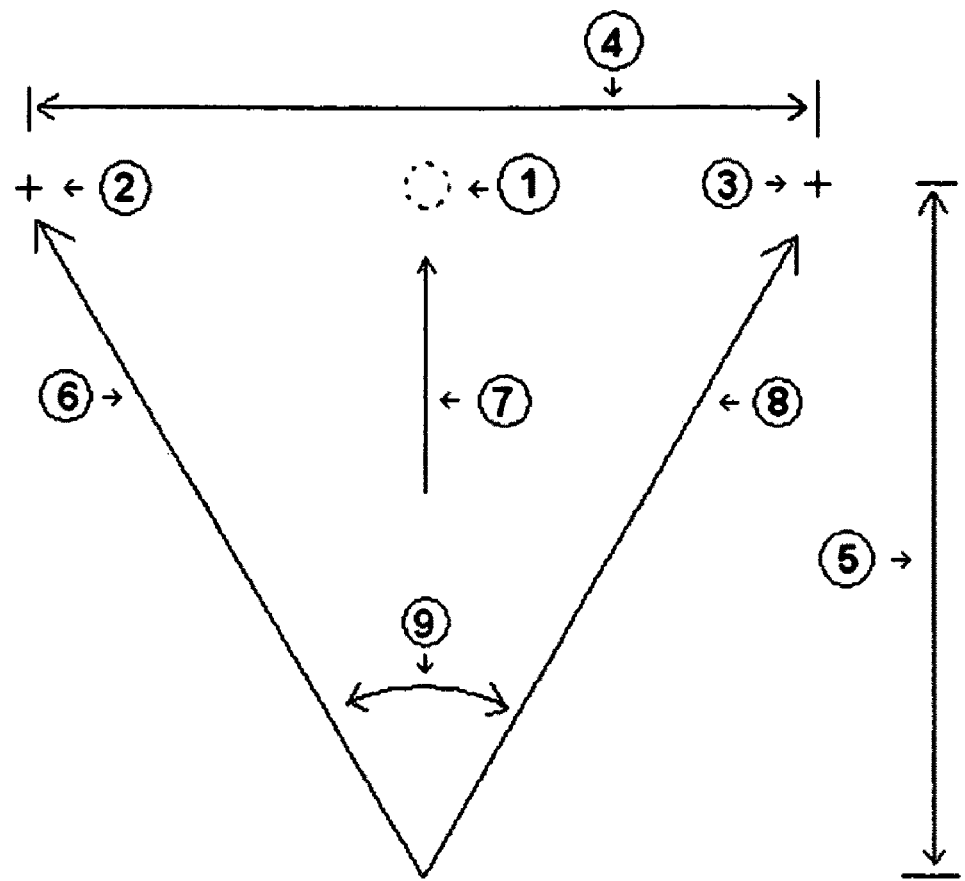
FIG. 1—Dynamic optotype computer image benchmark configuration.
Figure 2:
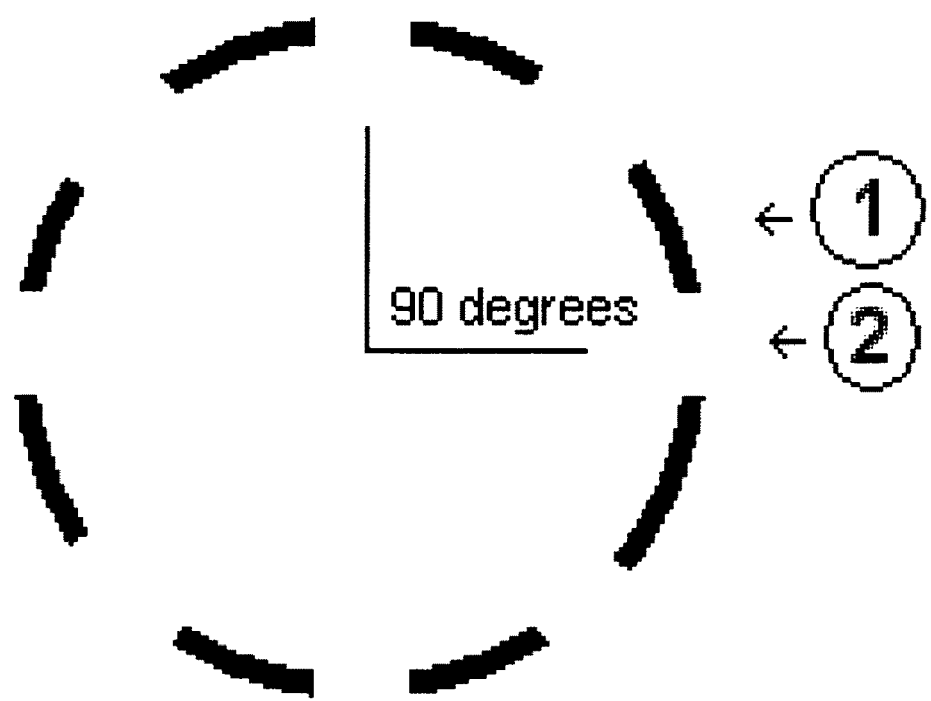

FIG. 2—Display of the dynamic optotype gap and segment height in circumferential degrees for a circular dynamic optotype. The sum of the circumferential degrees of the segment heights and gap heights will be 360 degrees.
Item 1—segment height.
Item 2—image gap height.

Figure 3:
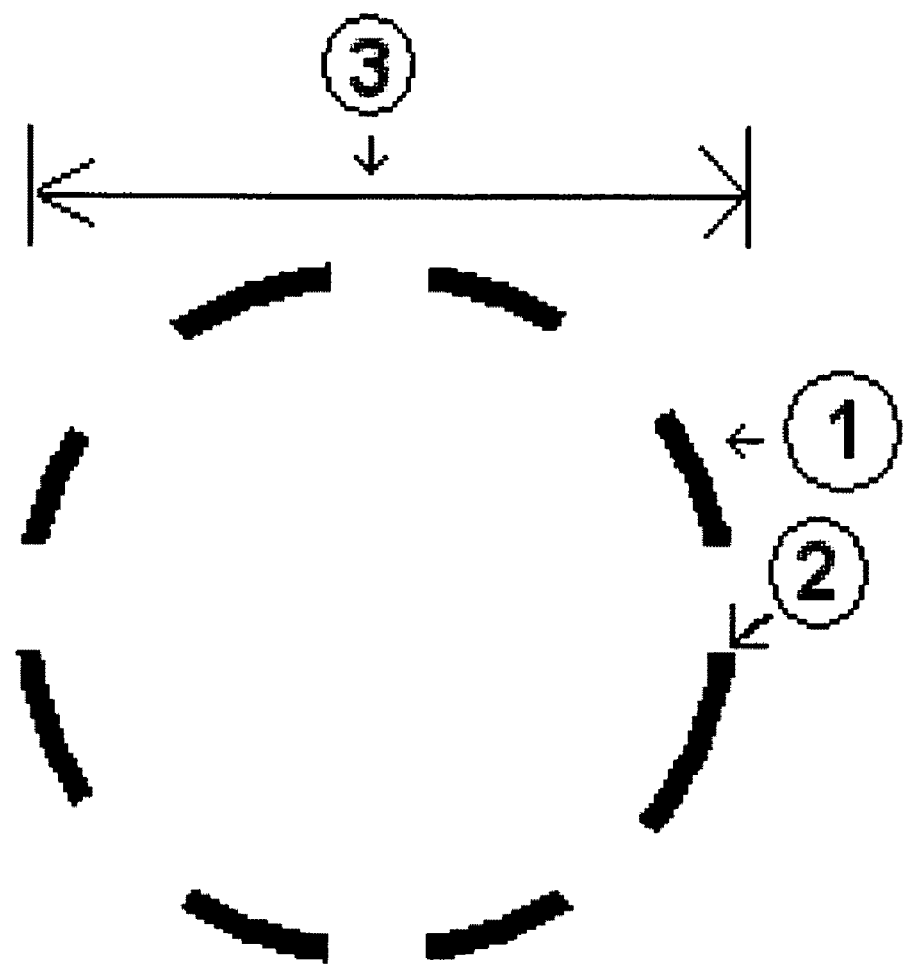

FIG. 3—Display of a typical segmented circular dynamic optotype with a gap (and segment) width (thickness) of approximately 4% as percent of the dynamic optotype diameter.
Item 1—dynamic optotype segment.
Item 2—dynamic optotype gap (and segment) width (thickness).
Item 3—dynamic optotype diameter.

Figure 4:
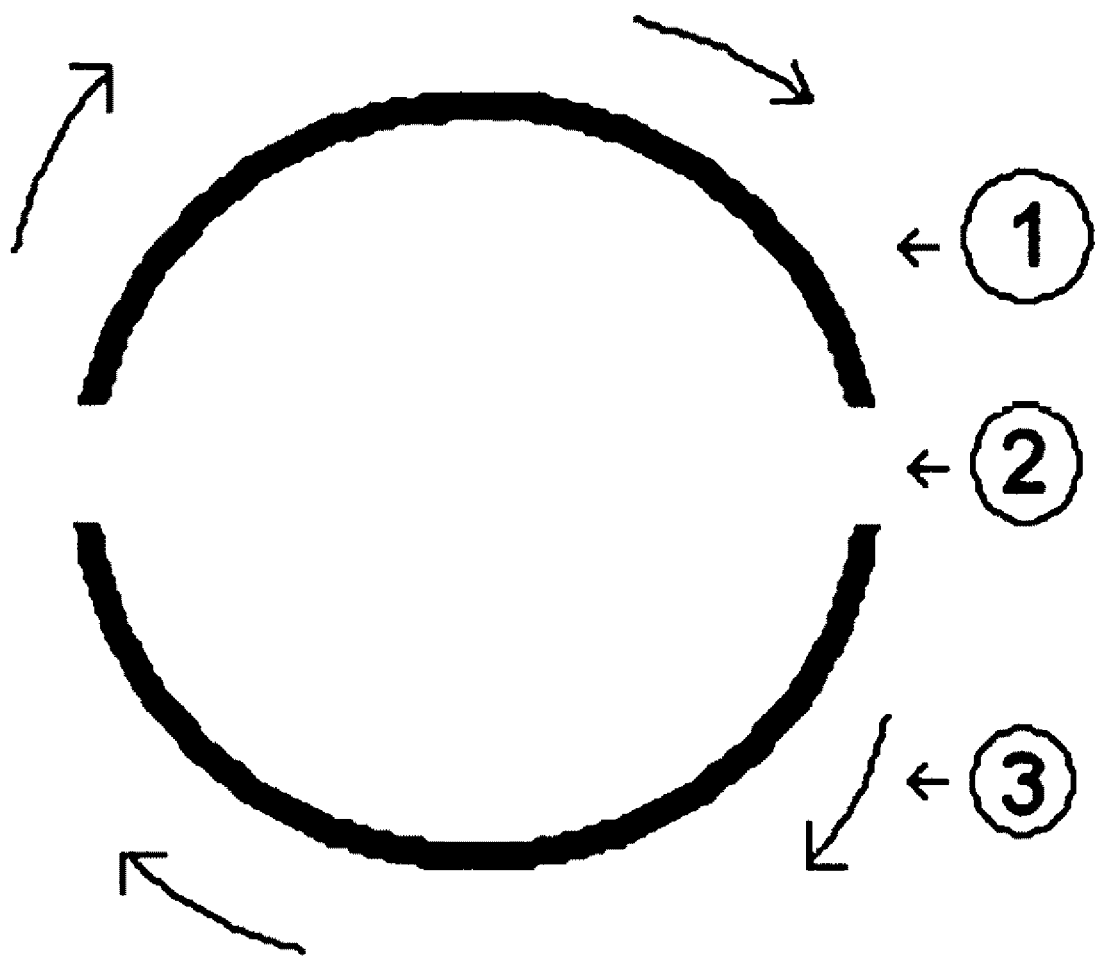

FIG. 4—Static image of a 2 segment animated dynamic optotype image rotating clockwise.
Item 1—image segment.
Item 2—image gap height.
Item 3—the clockwise direction of rotation of the image.

Figure 5:
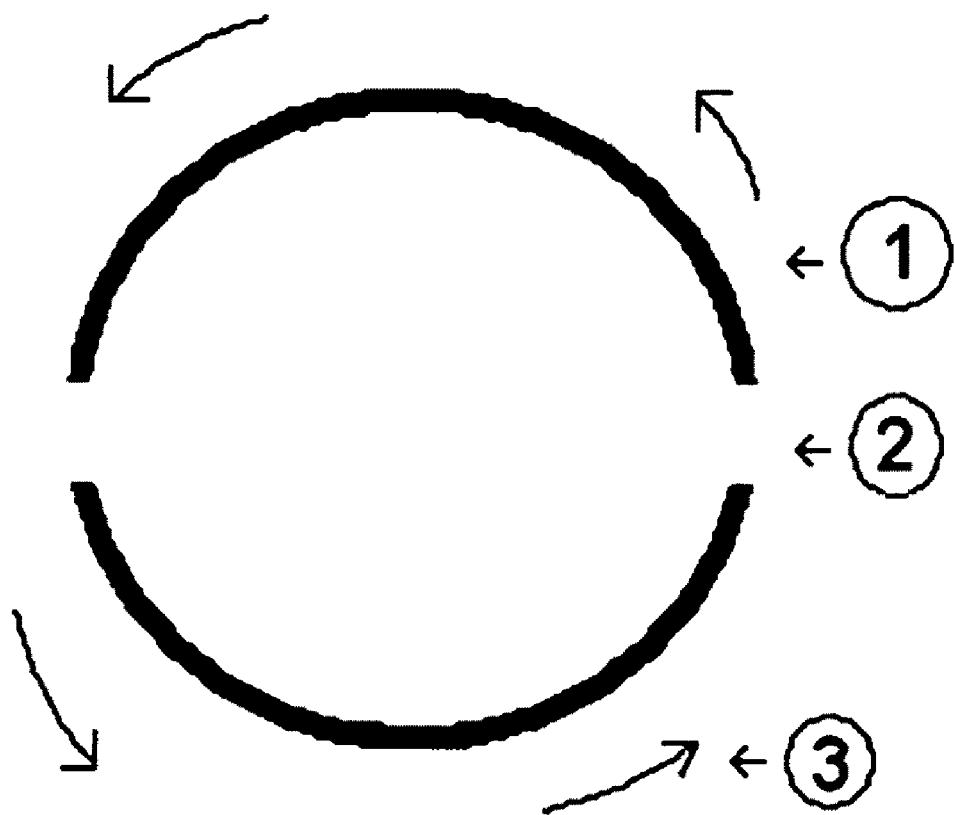

FIG. 5—Static image of a 2 segment animated dynamic optotype image rotating counter clockwise.
Item 1—image segment.
Item 2—image gap height.
Item 3—the counter clockwise direction of rotation of the image.

Figure 6:
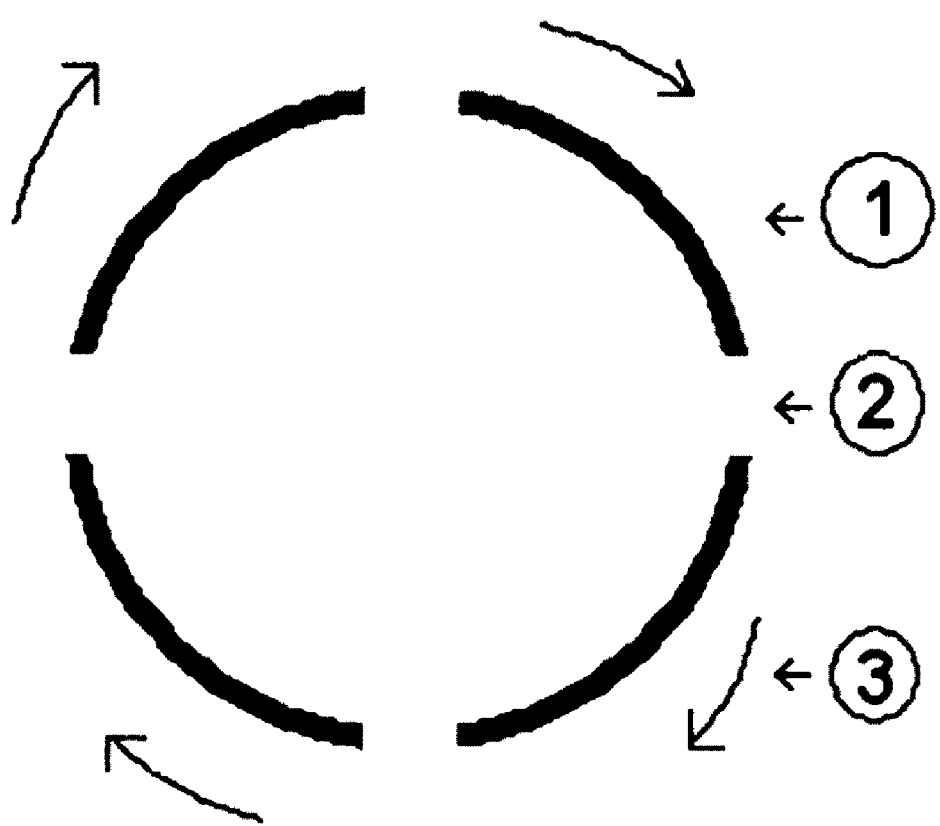

FIG. 6—Static image of a 4 segment animated dynamic optotype image rotating clockwise.
Item 1—image segment.
Item 2—image gap height.
Item 3—the clockwise direction of rotation of the image.

Figure 7:
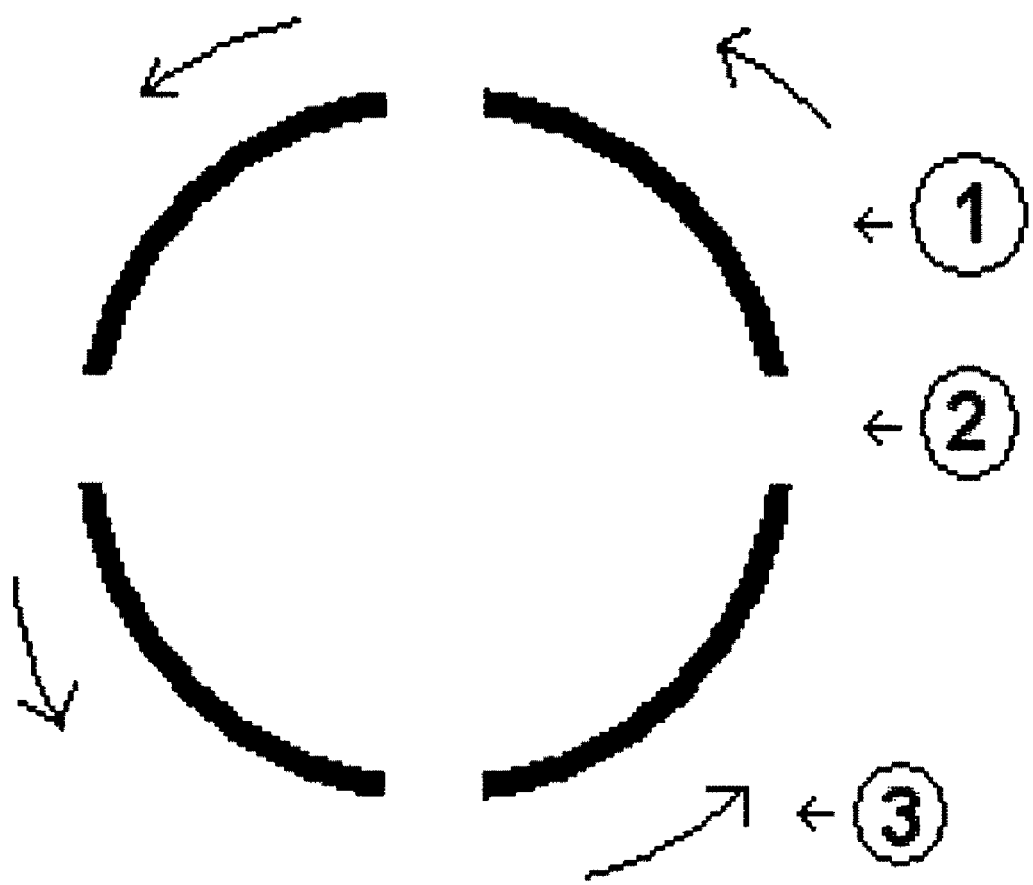

FIG. 7—Static image of a 4 segment animated dynamic optotype image rotating counter clockwise.
Item 1—image segment.
Item 2—image gap height.
Item 3—the counter clockwise direction of rotation of the image.

Figure 8:
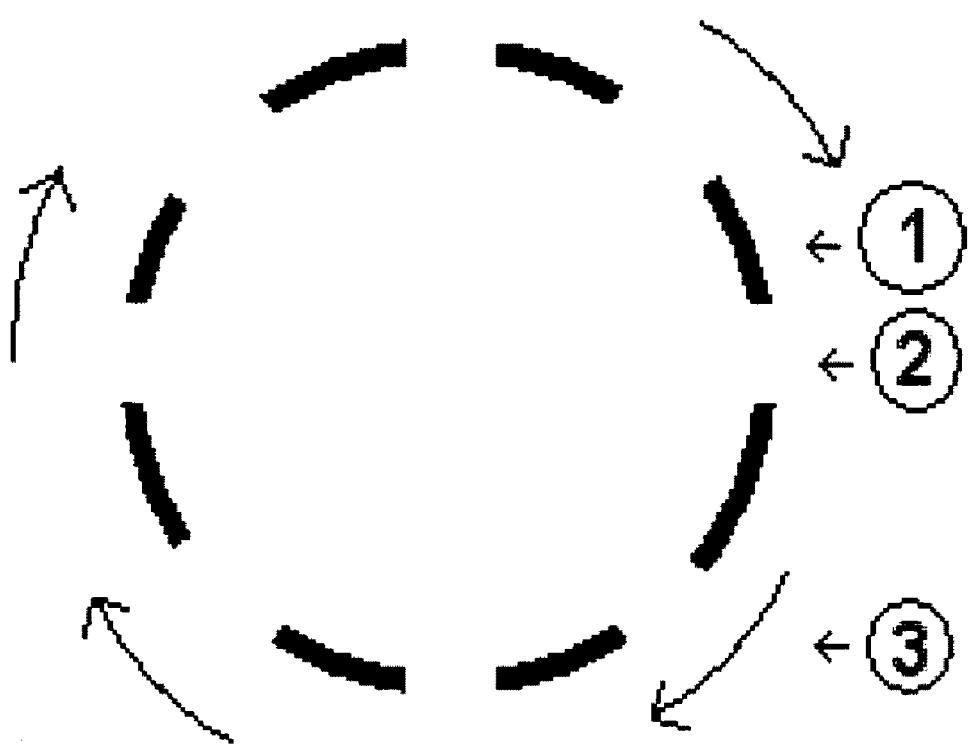

FIG. 8—Static image of an 8 segment animated dynamic optotype image rotating clockwise.
Item 1—image segment.
Item 2—image gap height.
Item 3—the clockwise direction of rotation of the image.

Figure 9:
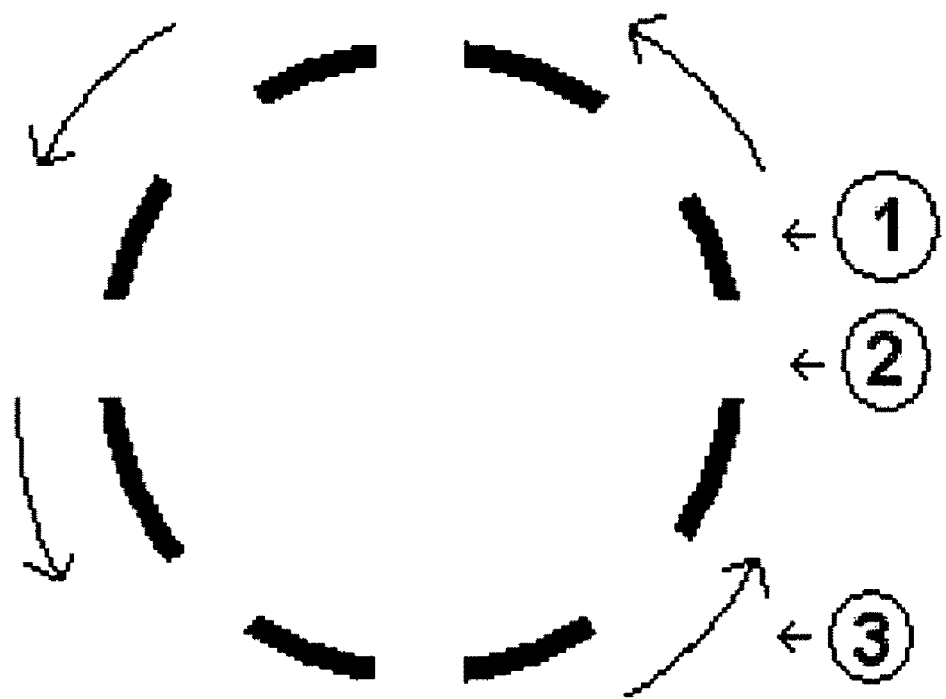

FIG. 9—Static image of an 8 segment animated dynamic optotype image rotating counter clockwise.
Item 1—image segment.
Item 2—image gap height.
Item 3—the counter clockwise direction of rotation of the image.

Figure 10:
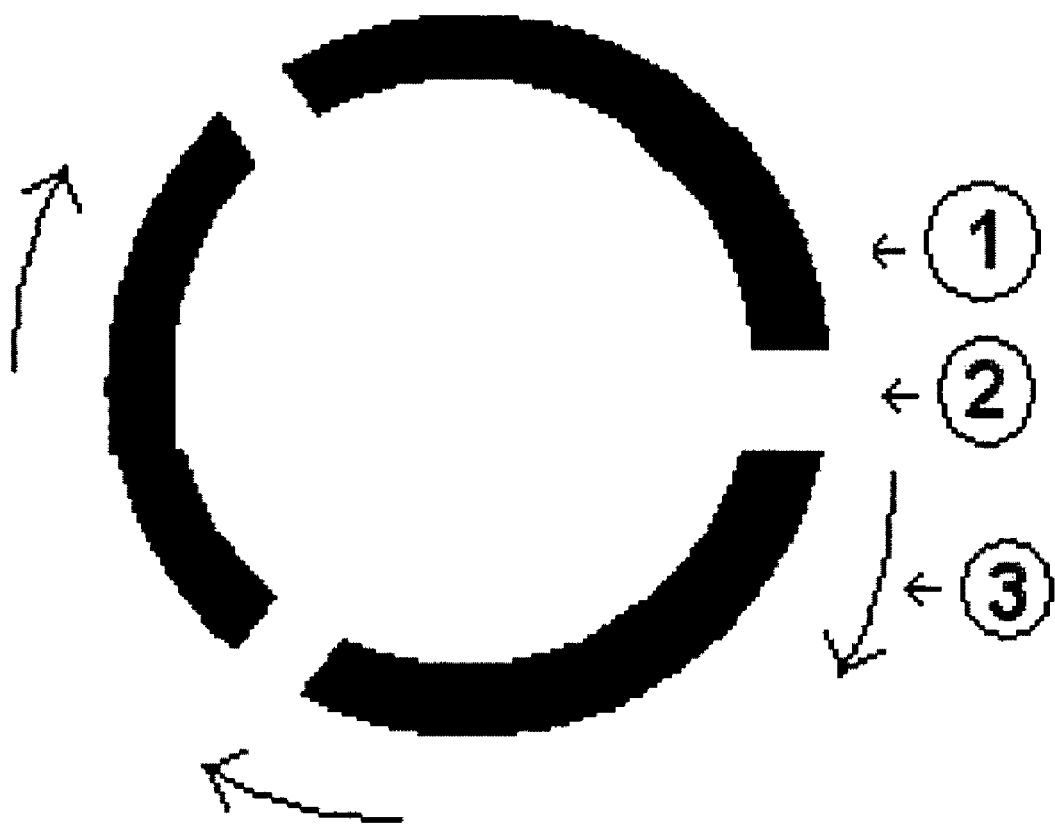

FIG. 10—Static image of a 3 segment animated dynamic optotype image rotating clockwise with a larger gap and segment width/thickness (approximately 10%).
Item 1—image segment.
Item 2—image gap height.
Item 3—the clockwise direction of rotation of the image.

Figure 11:
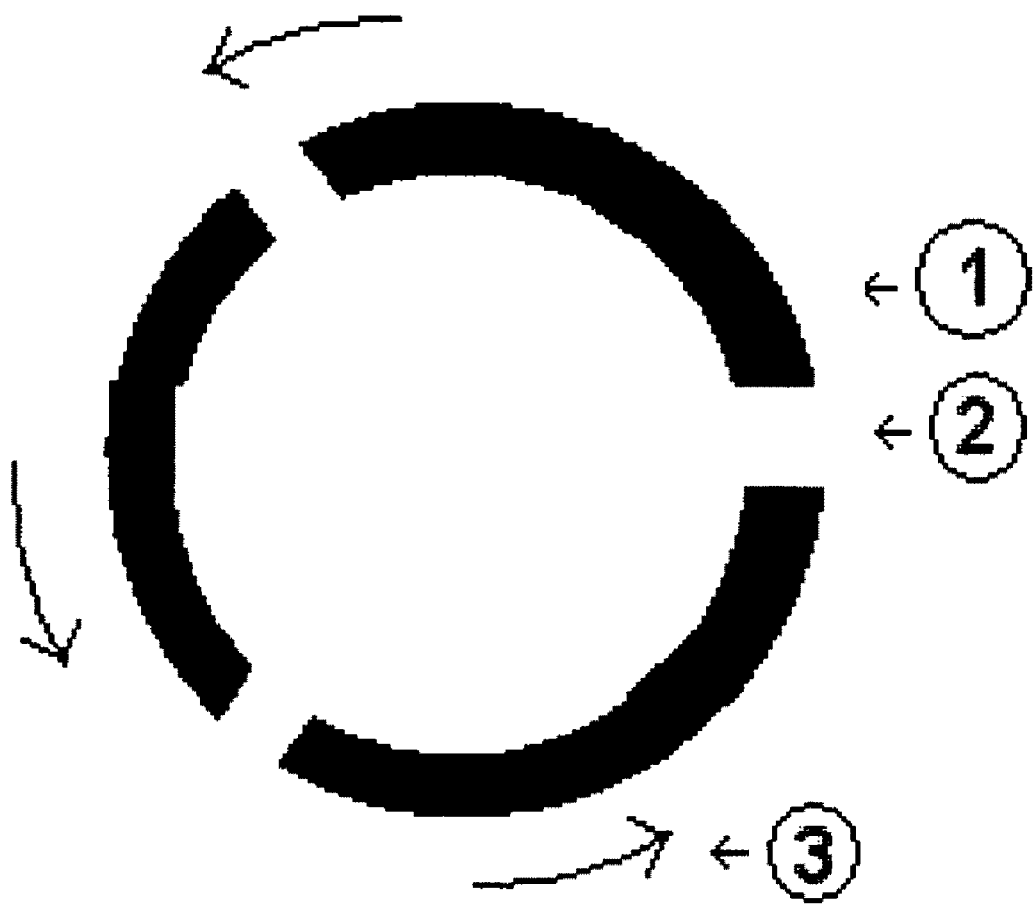

FIG. 11—Static image of a 3 segment animated dynamic optotype image rotating counter clockwise with a larger gap and segment width/thickness (approximately 10%).
Item 1—image segment.
Item 2—image gap height.
Item 3—the counter clockwise direction of rotation of the image.

Figure 12:
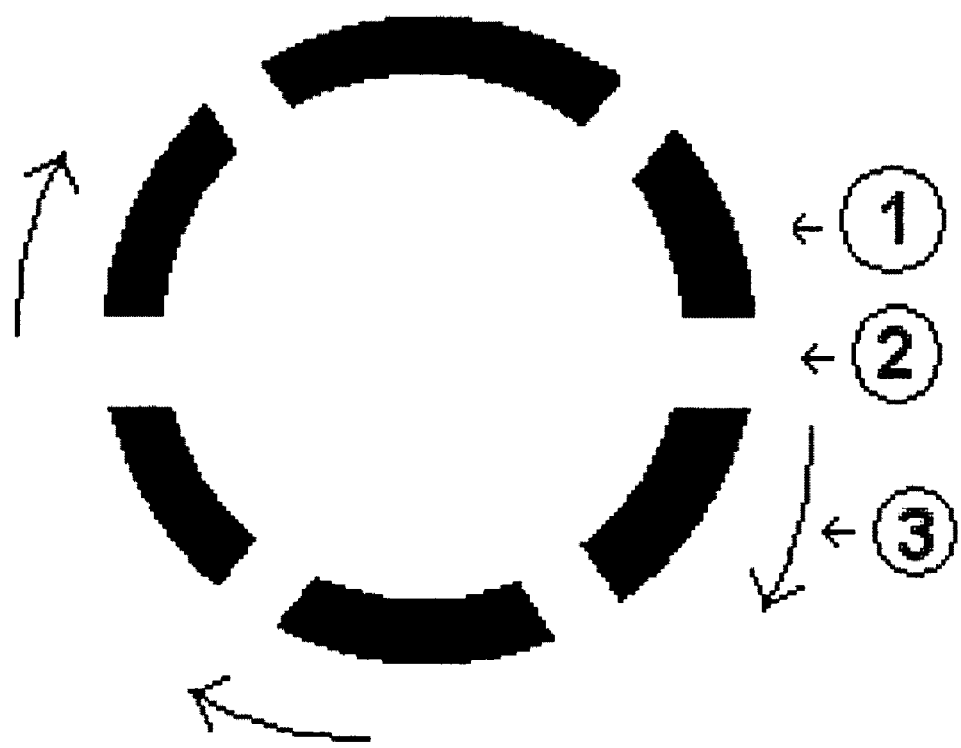

FIG. 12—Static image of a 6 segment animated dynamic optotype image rotating clockwise with a larger gap and segment width/thickness (approximately 10%).
Item 1—image segment.
Item 2—image gap height.
Item 3—the clockwise direction of rotation of the image.

Figure 13:
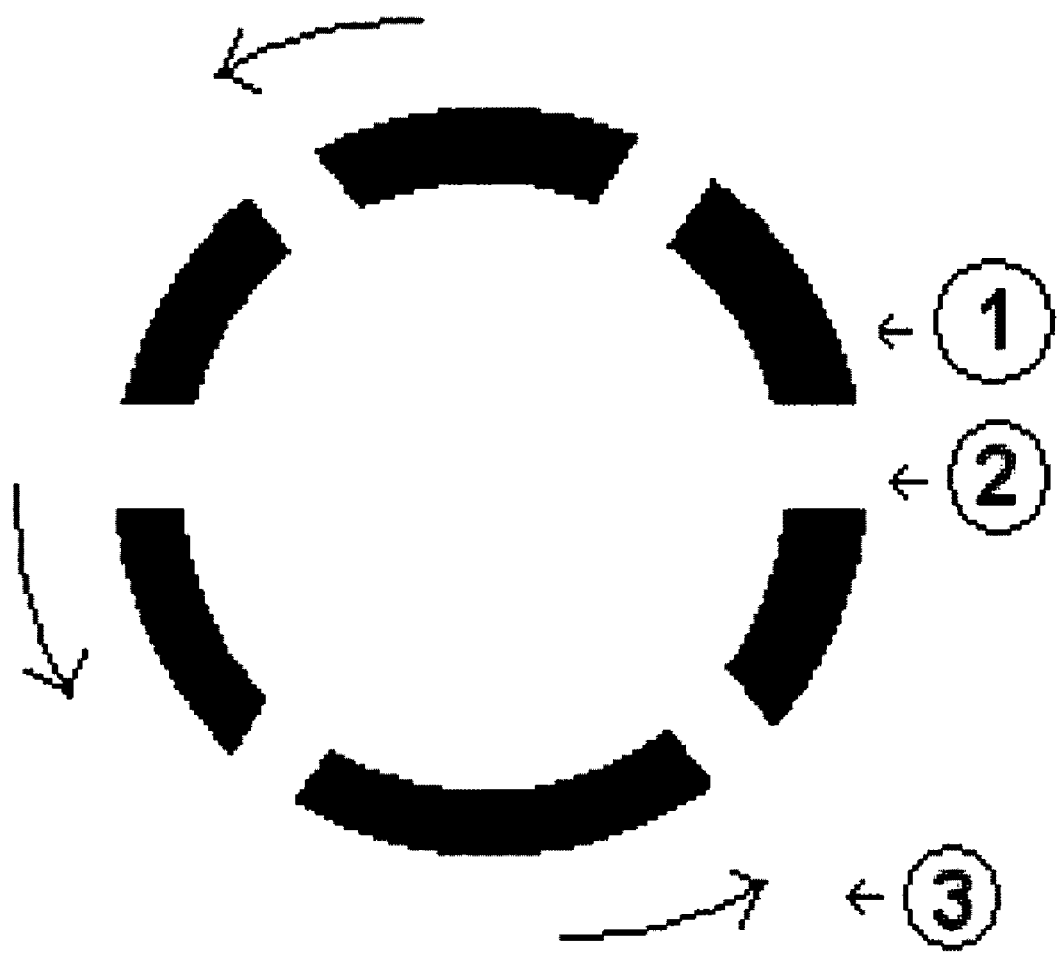

FIG. 13—Static image of a 6 segment animated dynamic optotype image rotating counter clockwise with a larger gap and segment width/thickness (approximately 10%).
Item 1—image segment.
Item 2—image gap height.
Item 3—the counter clockwise direction of rotation of the image.

Figure 14:
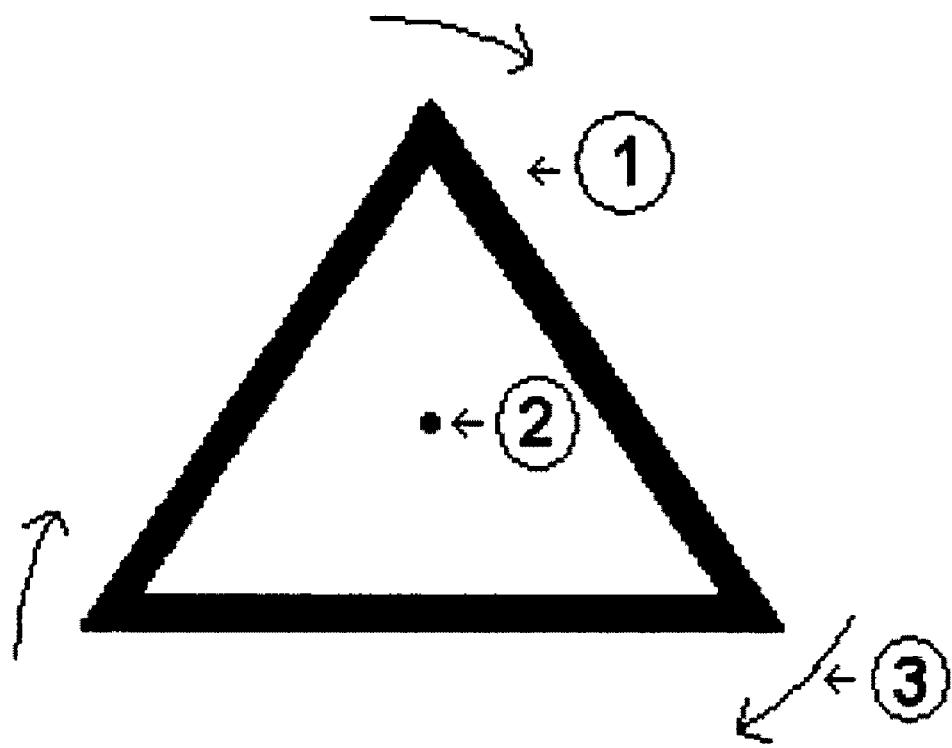

FIG. 14—Static image of a triangular animated dynamic optotype image rotating clockwise.
Item 1—image segment.
Item 2—center point of rotation.
Item 3—the clockwise direction of rotation of the image.

Figure 15:
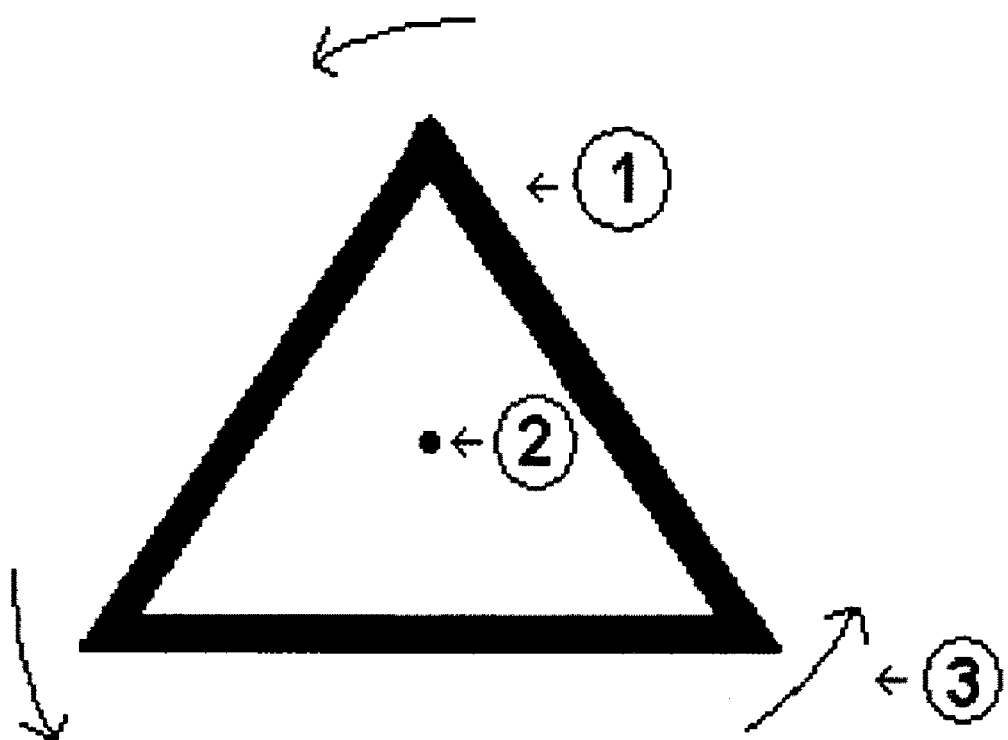

FIG. 15—Static image of a triangular animated dynamic optotype image rotating clockwise.
Item 1—image segment.
Item 2—center point of rotation.
Item 3—the clockwise direction of rotation of the image.

Figure 16:
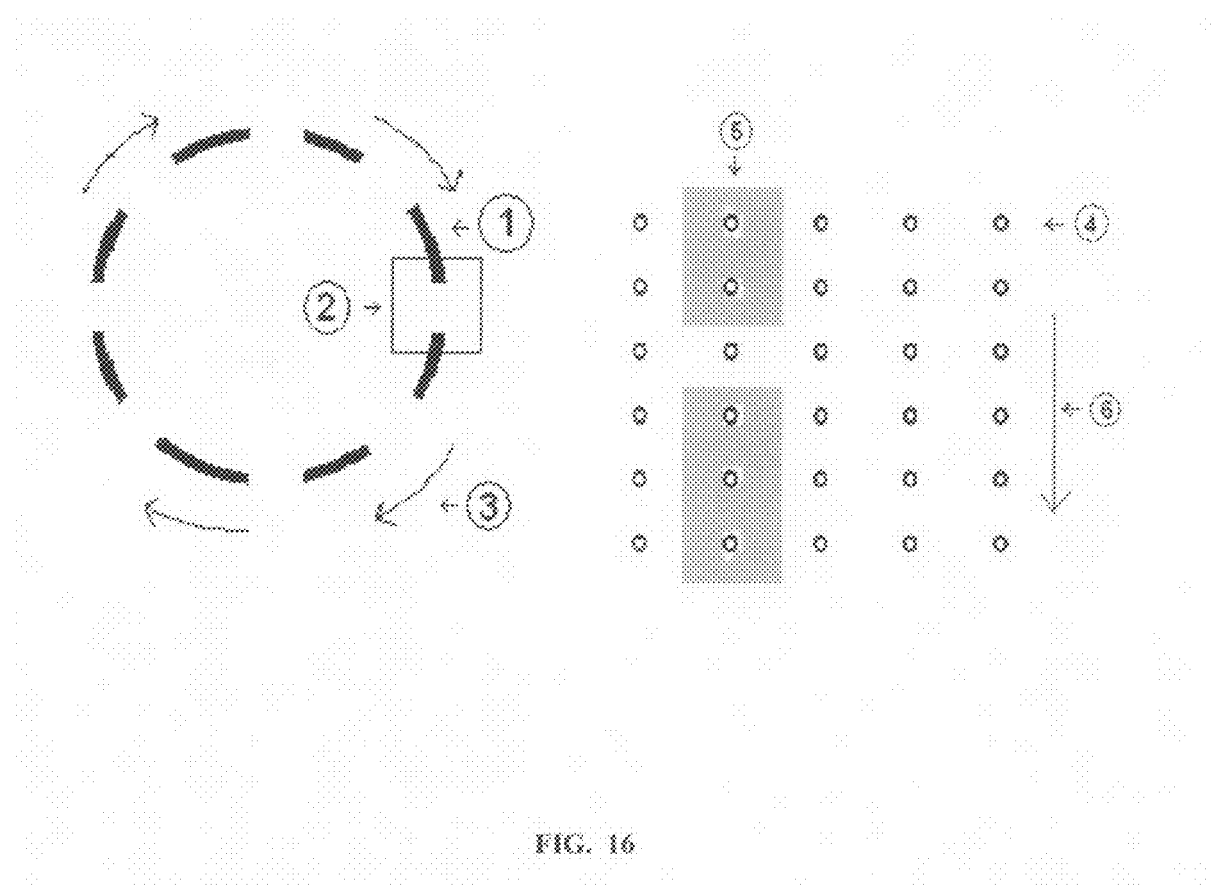

FIG. 16—Representation path of a thin segmented circular dynamic optotype image crossing the photoreceptors of the eye.
Item 1—image segment.
Item 2—thin gap (and segment) dynamic optotype image.
Item 3—clockwise direction of rotation of the image.
Item 4—representation of photoreceptor distribution.
Item 5—representative path of image gap across the photoreceptors.
Item 6—direction of motion of the dynamic optotype image gap.

Figure 17:
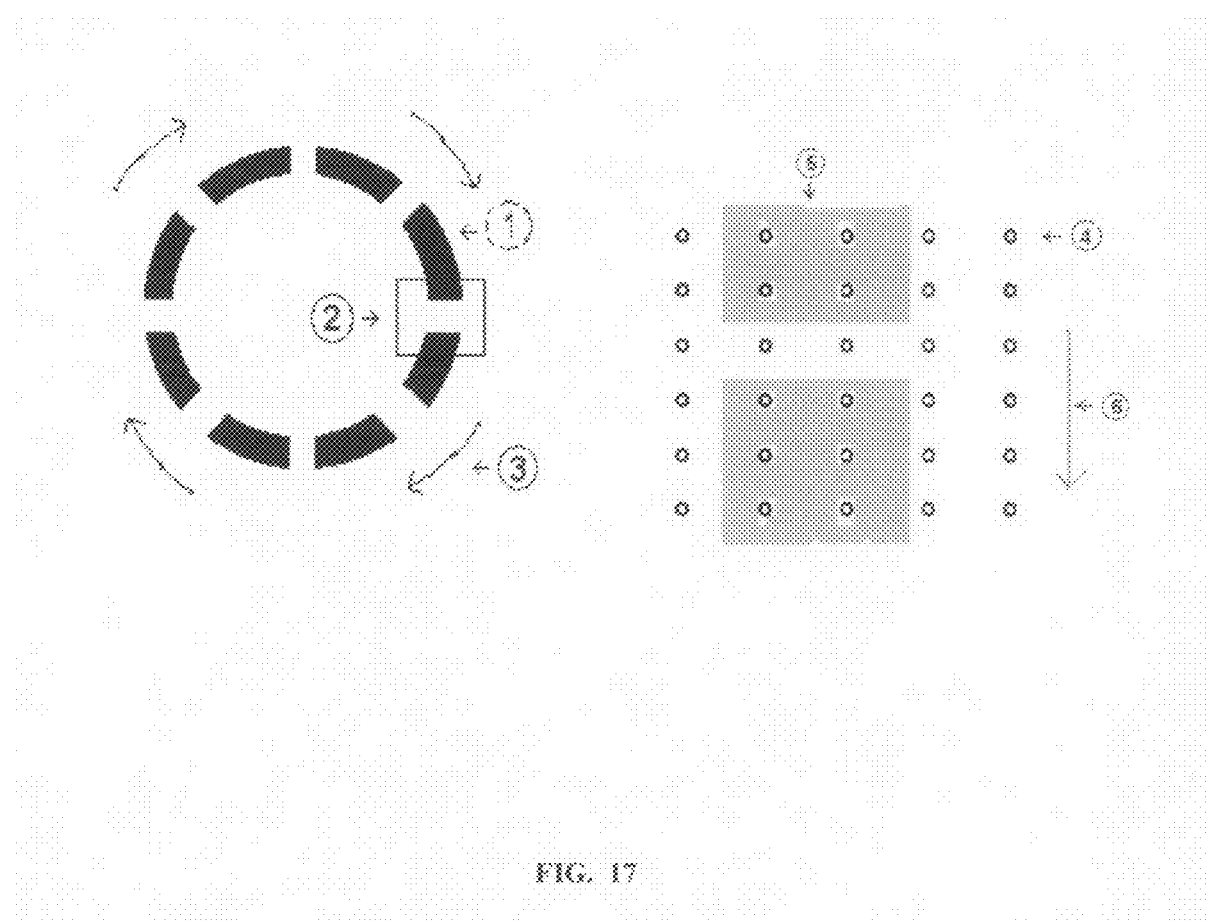

FIG. 17—Representation of path of a thick segmented circular dynamic optotype image crossing the photoreceptors of the eye.
Item 1—image segment.
Item 2—thick gap (and segment) dynamic optotype image.
Item 3—clockwise direction of rotation of the image.
Item 4—representation of photoreceptor distribution.
Item 5—representative path of image gap across the photoreceptors.
Item 6—direction of motion of the dynamic optotype image gap.

DETAILED DESCRIPTION OF THE INVENTION

The present invention creates a dynamic optotype that permits an accurate determination of acuity and allows patients to more accurately perceive visual acuity than they can by use of static reflected or projected letters, symbols, or shapes as used by the Snellen and similar tests. A dynamic optotype is a rotating geometric figure, such as a segmented circle, a triangle, or other shape having dimensions and a rotation rate such that its motion can just be perceived at a specified viewing distance by a subject whose vision is or has been corrected to the accepted 20/20 standard. Dynamic optotypes allow the patient to more accurately discern whether test images are either insufficiently or excessively magnified by the prescription optics thereby substantially improving the aforementioned prior art by providing a superior vision test chart and a method for rapidly and reliably testing a patient's ability to perceive image contrasts as a function of image size.

The novel test method uses animated dynamic optotype images (for example, one or more rotating segmented circles and shapes and colored dots of varying size, contrast, and color) on any type of visual display or projected image with the advantage of the dynamic optotype images creating an acuity threshold (at the refraction and distance from the dynamic optotype beyond which motion, either clockwise or counter-clockwise, is not perceivable). Dynamic optotypes also have an increased sharpness not available with the blurriness associated with projected or reflected static images. Unlike the Snellen or other static optotype tests, the patient does not rely on (the 60% accuracy of) guessing the identity of the letter(s) and shapes, but rather is able, based upon the appropriate refraction and distance from the animated image, to determine a precise acuity threshold for that dynamic optotype image.

That acuity threshold (perception of motion of a specific size image from a specific distance) correlates to the specific visual acuity. In looking at animated dynamic optotype images, the patient either sees the motion of the particularly sized dynamic optotype image because the viewing distance is close enough and the acuity refraction is sufficient, or the patient does not see the motion because the distance is too far and the acuity refraction is insufficient. This gives a much more accurate acuity threshold than is possible with the Snellen Test. Unlike the Snellen test, the subject does not need to be able to read English letters to identify the acuity threshold, and if the subject is able to identify the direction of motion of the dynamic optotypes, the subject does not even need to be able to read.

The variations in the size of the dynamic optotype images correspond to similar sized letters associated with the static images of the Snellen test, or static shapes of the Task test or the Landolt "C" test. The animated nature of the image shape (s) allows the patient to also avoid the subjective interpretive cognition of letters or symbols typical of the static Snellen type characters. The patient's perception of the acuity threshold of the motion of the animated dynamic optotype images, however, can be directly correlated to the refraction distance of the Snellen test.

The test is primarily designed to be viewed on a standard computer monitor or projected image at distances equivalent to and corresponding to the Snellen test. Typical dynamic optotype image dimensions (i.e. the diameter of rotating dynamic optotype segmented circles) that correspondence to the standard Snellen measurements are in Table 1. An 88 mm (~3.5 inch) high Snellen letter viewed at 6 meters (~20 feet) would typically have an acuity threshold equivalent to a rotating dynamic optotype segmented circle with a displayed screen diameter of 16 mm. The precise acuity threshold of a specific dynamic optotype as a ratio between the dynamic optotype diameter and the viewing distance (regardless of it measurement system) is determined by the shape, angular motion, rotation speed, gap width, gap height, color, background contrast, and image intensity. For example, in one preferred embodiment of the invention, a segmented circular dynamic optotype such as is shown in FIG. 2 can be employed

TABLE 1

| Snellen distance feet | Snellen distance meters | Snellen Letter Image Height Inches | Snellen Letter Image Height Millimeters | Typical Dynamic Optotype Image Diameter Millimeters |
|---|---|---|---|---|
| 60 | 24 | 14 | 352 | 48 |
| 30 | 12 | 7.0 | 176 | 24 |
| 20 | 6 | 3.5 | 88 | 16 |
| 10 | 3 | 1.75 | 44 | 8 |
| 5 | 1.5 | 0.87 | 22 | 4 |

Typical Dynamic Optotype Equivalents to Snellen Test Letter Heights

It is, therefore, a principal object of the present invention to provide an improved method for more accurately and more rapidly perceiving visual acuity. It is a further object of the invention to provide an improved vision test chart.

I claim:

1. A vision test comprising:
a projection surface;
at least one non-static rotating animated dynamic optotype image shape for measuring the visual acuity of a subject displayed upon the projection surface, the at least one non-static rotating animated dynamic optotype image shape having an image size, a plurality of image segments with image gaps between the image segments, the image segments having a segment size and a segment color, the image gaps having a gap separation distance;
a viewing distance between the at least one non-static rotating animated dynamic optotype image shape and a subject being tested for vision acuity;
a rate of rotation of the at least one non-static rotating animated dynamic optotype image shape;
a dynamic optotype viewing direction;
wherein the visual acuity of a subject is determined by varying at least one of the rate of rotation, the image size, the image segment size, the image gaps, and the image segment color;
a left fixation point;
a right fixation point;
a fixation point separation;
a left fixation point viewing direction; and
a right fixation point viewing direction; wherein the viewing distance is substantially equal to the viewing distance of a Snellen or Landolt vision test, the at least one non-static animated dynamic optotype image shape includes at least three image segments, with a fixation point separation distance of 26.2 cm, wherein the viewing distance is equal to 75 cm, and the fixation point separation angle is equal to 20 arc degrees.

* * * * *